United States Patent
Ciprian et al.

(10) Patent No.: US 7,074,926 B2
(45) Date of Patent: Jul. 11, 2006

(54) DECOLORATION AND COLOR STABILIZATION OF TEDA SOLUTION

(75) Inventors: Jürgen Ciprian, Ludwigshafen (DE); Matthias Frauenkron, Freinsheim (DE); Stephan Maurer, Böhl-Iggelheim (DE); Johann-Peter Melder, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 175 days.

(21) Appl. No.: 10/765,988

(22) Filed: Jan. 29, 2004

(65) Prior Publication Data

US 2004/0186291 A1    Sep. 23, 2004

(30) Foreign Application Priority Data

Jan. 30, 2003   (DE)   ................. 103 03 696

(51) Int. Cl.
*C07D 487/00*   (2006.01)

(52) U.S. Cl. .................................... 544/352
(58) Field of Classification Search ................ 544/352
See application file for complete search history.

(56) References Cited

U.S. PATENT DOCUMENTS

| | | | |
|---|---|---|---|
| 3,297,701 A | 1/1967 | Brader, Jr. et al. | 260/268 |
| 3,993,651 A | 11/1976 | Keating | 260/268 |
| 4,017,494 A | 4/1977 | Bosche et al. | 260/268 |
| 4,216,323 A | 8/1980 | Otsuki et al. | 544/352 |
| 4,463,320 A | 7/1984 | Dawson | 330/279 |
| 4,582,904 A | 4/1986 | Wells et al. | 544/178 |
| 4,757,143 A | 7/1988 | Vanderpool et al. | 544/352 |
| 4,804,758 A | 2/1989 | Hoelderich et al. | 242/18 |
| 5,741,906 A | 4/1998 | Santiesteban et al. | 544/352 |
| 6,552,194 B1 | 4/2003 | Lang et al. | 544/352 |
| 6,627,756 B1 | 9/2003 | Riechers et al. | 544/352 |

FOREIGN PATENT DOCUMENTS

| | | |
|---|---|---|
| DE | 24 42 929 | 3/1976 |
| DE | 26 11 069 | 9/1976 |
| DE | 28 49 993 | 5/1979 |
| DE | 37 18 395 | 12/1987 |
| DE | 36 34 258 | 4/1988 |
| EP | 111 928 | 6/1984 |
| EP | 382 055 | 8/1990 |
| EP | 831 096 | 3/1998 |
| EP | 842 935 | 5/1998 |
| EP | 842 936 | 5/1998 |
| EP | 952 152 | 10/1999 |
| EP | 1 070 717 | 1/2001 |
| EP | 1 223 172 | 7/2002 |

OTHER PUBLICATIONS

Hawley's Condensed Chemical Dictionary, 13th ed., revised by Richard J. Lewis, Sr, Van Nostrand Reinhold, p. 960, © 1997.*

Derwent JP 049048-609 (Abstract) 1972.

* cited by examiner

*Primary Examiner*—James O. Wilson
*Assistant Examiner*—Zachary C. Tucker
(74) *Attorney, Agent, or Firm*—Novak Druce Deluca & Quigg

(57) ABSTRACT

The present invention relates to a process for preparing TEDA solutions comprising a solvent selected from the group consisting of polyhydric alcohols and ethers of polyhydric alcohols. The process comprises passing gaseous TEDA into the solvent and subsequently treating the solutions with one or more suitable adsorbents. This gives solutions which have only low color numbers and are color-stable on storage. The solutions can be used as such in preferred applications of TEDA, preferably polyurethane production.

16 Claims, No Drawings

DECOLORATION AND COLOR STABILIZATION OF TEDA SOLUTION

The present invention relates to a process for preparing high-purity triethylenediamine (TEDA). In this process, TEDA is vaporized, this vapor is passed into a liquid solvent selected from the group consisting of polyhydric alcohols and ethers thereof and the solution obtained is brought into contact with an adsorbent selected from the group consisting of activated carbon and basic anion exchangers. The TEDA solution obtained has a low color number and can be used without further purification in customary applications.

TEDA is an important catalyst for the production of polyurethane foams. TEDA is a solid at room temperature. Various processes are known for its preparation and purification, including those which are disclosed in the following documents:

DT-A 24 42 929; U.S. Pat. No. 3,297,701; DE-A 36 34 258; DE-A 17 45 627; DE-A 37 18 395; EP-A 111 928; EP-A 382 055; EP-A 842 935; EP-A 842 936; EP-A 831 096; EP-A 952 152 and U.S. Pat. No. 5,741,906.

The processes known hitherto for preparing for TEDA lead to formation of product mixtures comprising TEDA together with water, by-products such as piperazine and high molecular weight compounds and also any solvent used in the reaction.

TEDA is usually separated off from these mixtures by batch or continuous distillation or rectification and is generally purified by crystallization or recrystallization in a subsequent step.

TEDA can be purified or handled without impairment of the quality, in particular the color and color stability, the odor and the purity, only with comparatively costly precautions.

The known, customary applications generally require a very pure, odorless and pure white TEDA. The patent applications mentioned below disclose processes which are said to give an appropriate TEDA quality:

DT-A 26 11 069; DE-A 28 49 993 and JP-A 49 048 609.

A disadvantage of these processes is that they do not give TEDA in the desired quality.

The patent application EP-A 1 070 717 of the applicant relates to a process for preparing pure TEDA in which TEDA is vaporized and the gaseous TEDA is passed into a liquid solvent and the TEDA is crystallized from the solution.

EP-A 1 223 172 of the applicant describes a process for preparing a solution of pure TEDA in which TEDA is vaporized from a mixture which further comprises a solvent or a diluent having a boiling point at atmospheric pressure in the range from 175 to 250° C. and the gaseous TEDA is passed into a liquid solvent. Subsequent crystallization of the TEDA from the solution obtained in this way gives pure TEDA of high quality.

The processes described in the two abovementioned patent applications of the applicant make it possible to obtain a TEDA of excellent purity and quality. The last process step. i.e. the crystallization of the TEDA from the solution obtained after the quench, is in some cases indispensable, for example when TEDA having a very high quality and purity is desired. If such a TEDA is to be present in solid form, this crystallization step or at least isolation of the TEDA from the solution is an obligatory process step and causes no further problems. However, TEDA is frequently used in the form of a solution in subsequent applications. For this purpose, the TEDA which has previously been crystallized from a solution has to be redissolved.

Many organic solvents are suitable as solvents for the TEDA quench. Examples include aliphatic, cyclic or acyclic hydrocarbons, in particular cyclic and acyclic, branched or unbranched alkane or alkane mixtures, for example n-pentane, i-pentane, cyclopentane, hexane, cyclohexane, heptane, octane and petroleum ether, chlorinated aliphatic hydrocarbons, in particular chlorinated alkanes, for example dichloromethane, trichloromethane, aromatic hydrocarbons, for example benzene, toluene and xylenes, chlorinated aromatic hydrocarbons, for example chlorobenzene, alcohols, for example methanol, ethanol, ethylene glycol, 1,4-butanediol and polyether alcohols, in particular polyalkylene glycols, for example diethylene glycol and dipropylene glycol, ketones, in particular aliphatic ketones, for example acetone, methyl ethyl ketone and diethyl ketone, aliphatic carboxylic esters, for example methyl acetate and ethyl acetate, aliphatic nitriles, for example acetonitrile and propionitrile, ethers, for example dioxane, THF, diethyl ether and ethylene glycol dimethyl ether and also mixtures of the abovementioned solvents.

As solvent for the TEDA quench, preference is given to using an aliphatic hydrocarbon or a polyalkylene glycol, in particular a saturated cyclic or acyclic, aliphatic hydrocarbon having from 5 to 8 carbon atoms, for example pentane, hexane, cyclohexane, heptane, monoethylene glycol, dipropylene glycol or 1,4-butanediol. The optional crystallization of the pure TEDA from the TEDA solution prepared according to the invention can be carried out by methods known to those skilled in the art. The TEDA crystals obtained by means of a subsequent multistage, preferably single-stage, crystallization are highly pure.

In the case of applications in which TEDA is used in the form of a solution, for example as catalyst in polyurethane production, the preferred solvent is a polyhydric alcohol or an ether. Preferred solvents from this group are dipropylene glycol (DGP), 1,4-butanediol (BDO) and monoethylene glycol (MEG).

When one of the abovementioned solvents is used, the gaseous TEDA cannot be quenched directly in this if purity and freedom from color have to meet high standards, since the resulting solution contains troublesome, color-imparting components and, in addition, in many cases becomes still darker on storage. For this reason, as described above, the TEDA is crystallized after the quench and is then redissolved in the desired alcohol or ether. If the purity has to meet high standards, the quench is preferably carried out using a lower aliphatic hydrocarbon such as pentane, hexane, cyclohexane, or heptane. After the quench, these solvents frequently give a TEDA solution which, owing to the solvent used, is not suitable for the desired applications and, furthermore, the color numbers obtained are not low enough to meet high standards.

For this reason, the TEDA has to be crystallized from the solutions obtained and then redissolved in a suitable solvent. It is clear that because of the many process steps to be carried out, if for no other reason, that it is desirable to have available a simple process for preparing TEDA solutions for applications such as polyurethane production.

It is an object of the present invention to provide a process for preparing TEDA solutions in alcohols and/or ethers which avoids the many process steps of the prior art. The solvents should preferably be selected from the group consisting of DPG, BDO and MEG. In particular, the process should make it possible to obtain a TEDA solution which meets requirements and has a low color number and a good storage stability by direct quenching in the desired solvent.

We have found that this object is achieved by a process fox preparing TEDA solutions comprising a solvent selected from the group consisting of polyhydric alcohols and ethers of polyhydric alcohols, which comprises a) passing gaseous TEDA into the solvent,
b) treating the solution with one or more absorbents.

In a preferred embodiment of the present invention, the polyhydric alcohol or the ether is selected from the group consisting of DPG, BDO and MEG. Furthermore, it is preferred that the TEDA solution be separated off from the adsorbents after contact with these.

It has been found that a highly pure TEDA solution in the solvents mentioned is obtained when after the TEDA has been vaporized and passed into the solvent (TEDA quench), the solution obtained is brought into contact with a suitable adsorbent.

In the processes known hitherto for recovering pure TEDA by means of a TEDA quench, the crude TEDA was vaporized, generally distilled. The TEDA obtained after the quench still contained impurities which made crystallization of the TEDA from the solution obtained necessary.

In contrast, the process of the present invention gives, after the quench and treatment with adsorbents, a solution which comprises a TEDA of high purity and can generally be used directly, for example as catalyst in polyurethane production. Naturally, the TEDA can also be isolated in solid form by crystallization from the solution obtained after the quench, but the advantages of the present invention in terms of a small number of process steps to be carried out are no longer achieved in this case. The TEDA which is obtainable in this way then has a high purity. Purities of >95%, preferably >99%, in particular >99.8%, are achieved in this way.

Up to the quench, the process of the present invention is carried out as described in the patent applications EP-A 1 070 717 and EP-A 1 223 172 of the applicant. The process steps of purification of TEDA by vaporization and quenching described in the patent applications mentioned are an integral part of the process of the present invention and are hereby incorporated by reference. The processes will be presented briefly below.

As a result of passing the gaseous TEDA into a liquid solvent (TEDA quench), the formation of undesirable by-products which lead to a reduction in quality is significantly reduced.

The gaseous TEDA is passed into the liquid solvent in a quenching apparatus, preferably a falling film condenser (thin film, trickle film or falling stream condenser) or in a nozzle apparatus. The gaseous TEDA can be conveyed in cocurrent or in countercurrent to the liquid solvent. It is advantageous to introduce the gaseous TEDA into the quenching apparatus from the top. Tangential introduction of the liquid solvent at the top of the falling film condenser or introduction of the liquid solvent through one or more nozzles in order to achieve complete wetting of the interior wall of the quenching apparatus are also advantageous.

The amount of solvent used is chosen from the point of view of effectiveness and convenience. In general, the amount is chosen so that, depending on the type of solvent, solutions having a TEDA content of from about 1 to 50% by weight, preferably from 20 to 40% by weight, are obtained.

In general, the temperature in the TEDA quench is set by bringing the solvent used and/or the quenching apparatus to a temperature in the range from 20 to 100° C., preferably from 30 to 60° C.

The absolute pressure in the TEDA quench is generally from 0.5 to 1.5 bar.

If the TEDA to be purified is vaporized from a mixture with a solvent or diluent as described in EP-A 1 223 172, the solvent or diluent preferably has a boiling point at atmospheric pressure of from 180 to 250° C., more preferably from 180 to 250° C., in particular from 190 to 210° C.

As solvents or diluents present in the mixture from which the TEDA is vaporized, the following are particularly useful:

inert polar aprotic solvents such as alkyl-2-pyrrolidones, for example N-methy-2-pyrrolidone (NMP), 1-ethyl-2-pyrrolidone, 1,5-dimethyl-2-pyrrolidone, 1-isopropyl-2-pyrrolidone, ethers, for example diethylene glycol diethyl ether, triethylene glycol dimethyl ether and triethylene glycol diethyl ether, ketones, for example acetophenone and propiophenone, lactones, for example γ-butyrolactone, sulfoxides, for example dimethyl sulfoxide, carboxylic esters, for example dimethyl fumarate, nitriles, for example benzonitrile, and ureas, for example 1,3-dimethylimidazolidin-2-on (DMEU) and tetramethylurea, inert cyclic or acyclic hydrocarbons, in particular saturated cyclic or acyclic hydrocarbons, for example undecane, dodecane, cis-decalin and trans-decalin, inert chlorinated aliphatic hydrocarbons such as 1-chlorooctane and 1,1-dichlorooctane, inert aromatic hydrocarbons, nitroaromatics and phenols, for example naphthalene, n-butylbenzene, phenol, cresol, nitrobenzene and nitrophenol, inert chlorinated aromatic hydrocarbons, for example 1,2-dichlorobenze, benzyl chloride, 1,2,3,4-tetramethylbenzene and 1,2,3,5-tetramethylbenzene, inert alcohols, for example benzyl alcohol, 2-ethylhexanol, 1-octanol, i-decanol, 1,2-propanediol, 1,3-propanediol, ethylene glycol, diethylene glycol, 1,2-propylene glycol, 1,3-propylene glycol, 1,2-butanediol, 1,3-butanediol, 2,3-butanediol, 1,4-butanediol, neopentyl glycol, diethylene glycol monomethyl ether and dipropylene glycol, inert primary, secondary and tertiary amines, for example tri-n-butylamine, benzylamine, aniline, N-ethylaniline, N,N-dimethylaniline and N,N-diethylaniline, inert N-alkylamides, for example N-methylformamide and N-methylacetamide and mixtures thereof.

Particular preference is given to polar aprotic solvents or diluents having an $E^N_T$ of from 0.1 to 0.6, especially from 0.2 to 0.5, in particular from 0.3 to 45.

(For the definition of $E^N_T$, see Ch. Reichardt, Solvents and solvent effects in organic chemistry, 2nd edition, VHC 1988).

Very particularly preferred solvents are NMP and ethylene glycol.

The solvent or diluent can be used in a single pass or as a circulating solution.

The amount of solvent or diluent used is chosen from the point of view of effectiveness and convenience. In general, the amount used is, depending on the type of solvent or diluent, such that solutions or mixtures having a TEDA content of from about 1 to 90% by weight, preferably from 40 to 70% by weight, are obtained.

The vaporization of the TEDA, optionally from a mixture of this with a solvent or diluent, can be carried out by methods and under conditions with which those skilled in the art are familiar, e.g. in a distillation or rectification apparatus into which the TEDA is placed, if applicable together with the solvent or diluent.

The TEDA to be purified can be obtained by known processes, e.g. by reaction of monoethanolamine, diethanolamine, triethanolamine, ethylenediamine, diethylenetriamine, triethylenetetramine, piperazine, N-(2-hydroxyethyl) piperazine, N,N'-bis(2-hydroxyethyl)piperazine, N-(2-aminoethyl)piperazine, N,N'-bis(2-aminoethyl)piperazine, morpholine or mixtures thereof over a catalyst, for example metal pyrophosphates, metal phosphates, for example an alkaline earth metal monohydrogenphosphate, zeolites, zirconium phosphates, $Al_2O_3$, $SiO_2$, phosphorus-containing $TiO_2$ or $ZrO_2$, at elevated temperature, generally from 250 to 450° C. The pressure in the reaction is usually from 0.1 to 50 bar, in particular from 0.1 to 5 bar. The reaction can optionally be carried out in the presence of an inert polar aprotic solvent such as an N-alkylpyrrolindone, for example N-methypyrrolidone, dioxane, THF, a dialkylformamide, for example dimethylformamide, a dialkylacetamide, for example dimethylacetamide, and an inert carrier gas, for example $N_2$ or Ar.

If desired, the TEDA can be crystallized and separated off by solid-liquid separation.

In contrast to known processes, according to the present invention the quench is carried out in a solvent selected from the group consisting of polyhydric alcohols and ethers of these alcohols. Examples of such alcohols include ethanediol, 1,2-propanediol, 1,3-propanediol, 1,2-butanediol, 1,3-butanediol, 1,4-butanediol, glycerol, diethylene glycol, triethylene glycol, dipropylene glycol, tripropylene glycol, trimethylolpropane.

In the case of the ethers of the polyhydric alcohols, all hydroxyl. groups can be etherified, but it is also possible for not all of the hydroxyl groups to be etherified, for example in the form of monoethers. The ethers of the polyhydric alcohols are generally derived from lower monohydric alcohols, for example methanol or ethanol, in particular methanol.

The most preferred solvents for the TEDA quench are selected from the group consisting of monoethylene glycol (MEG), dipropylene glycol (DPG) and butanediol (BDO).

In most cases, the solution obtained after the quench contains color-imparting components and troublesome odoriferous substances and can for this reason not be used directly in most applications, in particular polyurethane production. Furthermore, a further darkening of the solution is observed on storage, and this results in a further deterioration in the quality of the TEDA solution. The process of the present invention makes it possible to remove the color-imparting components and the odoriferous components and to stabilize the solution so that further darkening occurs to only aminor extent, if at all.

This is achieved, according to the present invention, by contact with one or more suitable adsorbents. The adsorbents are preferably selected from the group consisting of basic anion exchangers and activated carbons.

In particular, the adsorbents are selected from the group consisting of strongly basic anion exchangers and activated carbons which are suitable for use in the liquid phase.

For the purposes of the present invention, the term "strongly basic anion exchanger" refers to an ion exchanger which contains functional groups, preferably $Cl^-$, $OH^-$ or $SO_4^-$.

If activated carbon is used, it can be present in the form of powdered carbon or granulated carbon.

Preferred activated carbons should have a specific surface area of from 400 to 3 000 $m^2/g$, in particular from 700 to 1 500 $m^2/g$.

Examples of suitable grades of activated carbon are those marketed under the following trade names:
Carbo Tech PAK 1220, from Carbo Tech,
Chemviron CAL, from Chemviron,
CPG LF 1240, from Chemviron,
F300, F400, from Chemviron.

Examples of suitable basic anion exchangers are those marketed under the following trade names.
Ambersep 9000H (from Rohm & Haas), MonoPlus M500, MonoPlus MP500, MonoPlus MP62, MonoPlus MP64, MonoPlus M600, MonoPlus M610 (each from Bayer AG), Ambedjet 4200, Amberlite IRA404 (each from Rohm & Haas).

It is possible to use a single activated carbon or activated carbon grade or a combination of two or more activated carbons or activated carbon grades.

Likewise, it is possible to use a single basic anion exchanger or a combination of basic anion exchangers.

In a preferred embodiment of the present invention, a combination of at least one activated carbon and at least one basic anion exchanger is used. It has been found that this gives improved decolorizing performance. The activated carbon and the basic anion exchanger can be added together or in succession in any order. Preference is given to adding the adsorbents together or adding the activated carbon before the anion exchanger. Particular preference is given to adding the activated carbon before the anion exchanger.

An advantage of the combined use of activated carbon and a basic anion exchanger is that this cannot only significantly reduce the color number of the respective batch but also increases the color number stability on storage.

The temperature at which the treatment according to the present invention of the TEDA solution with the adsorbents is carried out ranges from 10 to 90° C., preferably from 20 to 80° C., in particular from 30 to 70° C.

The process of the present invention can be carried out by adding the adsorbent/adsorbents to the respective batch and bringing the TEDA solution and the adsorbent(s) into intimate contact with one another, for example by stirring or shaking. The adsorbent is then preferably separated off.

In a preferred embodiment of the present invention, the adsorbents are installed in the form of a fixed bed and the solution to be decolorized is passed over the fixed bed. The adsorbents can also be in the form of a melt bed or a fluidized bed.

The process can be carried out continuously, semicontinuously or batchwise. The preferred continuous embodiment is that in fixed beds in a carousel arrangement, in particular with regeneration. The preferred semicontinuous embodiment is that in two alternately operated fixed beds. In a batch process, all steps of the process are preferably carried out in succession in a fixed bed.

In a preferred embodiment of the process of the present invention, exhausted adsorbent is regenerated, thus making reuse or recirculation in the process possible. Regeneration both of the activated carbon and of the basic anion exchanger can be carried out using strong mineral acids and strong caustic alkalis. Examples are HCl in various concentrations, for example 5 and 10%, and strong caustic alkalis, for example NaOH and KOH, in various concentrations, for example 5 and 10%. Regeneration of the adsorbents can be carried out continuously, semicontinuously or batchwise.

The invention is illustrated by the following examples.

EXAMPLE 1

A 33% strength solution of TEDA in dipropylene glycol which had been obtained by quenching and had a color number of about 300 APHA was shaken with the indicated amounts (based on 100 g of solution) of the respective activated carbon for 23 hours. The results are shown in table 1 below.

|  | | Sorbent | | Amount in g per 100 g of solution | Color number APHA |
|---|---|---|---|---|---|
|  | | Type | Grade | | |
| Batch I | | | | | 357 |
| 1 | Granules | Activated carbon | D43/1 | 1.02 | 366 |
| 2 | Granules | Activated carbon | D43/1 | 2.95 | 288 |
| 3 | Granules | Activated carbon | D43/1 | 4.89 | 247 |
| 4 | Granules | Activated carbon | CPG LF 12 × 40 | 1.00 | 343 |
| 5 | Granules | Activated carbon | CPG LF 12 × 40 | 2.96 | 250 |
| 6 | Granules | Activated carbon | CPG LF 12 × 40 | 4.83 | 203 |
| 7 | Granules | Activated carbon | Chemviron CAL | 0.98 | 322 |
| 8 | Granules | Activated carbon | Chemviron CAL | 2.92 | 307 |
| 9 | Granules | Activated carbon | Chemviron CAL | 4.85 | 191 |
| Batch II | | | | | 311 |
| 10 | Powder | Activated carbon | PAK 1220 | 5.13 | 69 |
| 11 | Granules | Activated carbon | ROW 0.8 supra | 5.07 | 120 |
| 12 | Powder | Activated carbon | CAL milled | 5.19 | 70 |
| 13 | Powder | Activated carbon | F300 milled | 5.05 | 92 |
| 14 | Powder | Activated carbon | Carbopal PC 250 | 5.10 | 133 |
| 15 | Powder | Activated carbon | Carbopal M3 | 5.52 | 99 |
| 16 | Granules | Molecular sieves | MS 10 A | 4.68 | 316 |
| 17 | Granules | Adsorbent resin | XAD4 | 5.28 | 325 |
| Batch III | | | | | 402 |
| 18 | Powder | Activated carbon | PAK 1220 | 1.02 | 166 |
| 19 | Powder | Activated carbon | PAK 1220 | 3.00 | 94 |
| 20 | Powder | Activated carbon | PAK 1220 | 5.00 | 66 |
| 21 | Powder | Activated carbon | PAK 1000 | 1.08 | 220 |
| 22 | Powder | Activated carbon | PAK 1000 | 3.06 | 173 |
| 23 | Powder | Activated carbon | PAK 1000 | 5.07 | 151 |
| 24 | Granules | Zeolite | DAY | 1.05 | 401 |
| 25 | Granules | Zeolite | DAY | 3.06 | 409 |
| 26 | Granules | Zeolite | DAY | 5.02 | 414 |
| 27 | Strongly acidic | Ion exchange resin | Amberlite 252 RFH | 1.01 | 375 |
| 28 | Strongly acidic | Ion exchange resin | Amberlite 252 RFH | 3.05 | 388 |
| 29 | Strongly acidic | Ion exchange resin | Amberlite 252 RFH | 5.11 | 421 |
| 30 | Strongly acidic | Ion exchange resin | Amberlite 252 RFH | 1.02 | 366 |
| 31 | Strongly acidic | Ion exchange resin | Amberlite 252 RFH | 3.05 | 372 |
| 32 | Strongly acidic | Ion exchange resin | Amberlite 252 RFH | 5.18 | 343 |
| 33 | Strongly basic | Ion exchange resin | Ambersep 900 OH | 1.00 | 126 |
| 34 | Strongly basic | Ion exchange resin | Ambersep 900 OH | 3.02 | 109 |
| 35 | Strongly basic | Ion exchange resin | Ambersep 900 OH | 4.99 | 98 |
| 36 | Weakly basic | Ion exchange resin | Lewatit MP 62 WS | 1.05 | 379 |
| 37 | Weakly basic | Ion exchange resin | Lewatit MP 62 WS | 3.01 | 389 |
| 38 | Weakly basic | Ion exchange resin | Lewatit MP 62 WS | 5.15 | 392 |
| 39 | Granules | Silica gel | Sylobead B127 | 1.11 | 379 |
| 40 | Granules | Silica gel | Sylobead B127 | 3.07 | 385 |
| 41 | Granules | Silica gel | Sylobead B127 | 5.00 | 391 |
| 42 | Granules | Silica gel | Sylobead W127 | 1.05 | 385 |
| 43 | Granules | Silica gel | Sylobead W127 | 3.04 | 396 |
| 44 | Granules | Silica gel | Sylobead W127 | 5.01 | 399 |

The amount indicated in each case of 33% strength quench solution of TEDA in DPG was admixed with the respective amount of adsorbent (activated carbon, basic anion exchanger or a combination thereof) and shaken for 24 hours at 60° C. The results are shown in table 2.

| Experiment | Amount of TEDA solution/g | Adsorbent | Amount/g | APHA color number obtained |
|---|---|---|---|---|
| A | 50.529 | Ambersep 900 OH | 2.551 | 33.8 |
| B | 50.092 | PAK 1200 | 2.598 | 94.5 |
| C | 100.236 | Ambersep 900 OH + PAK 1220 | 2.572/2.541 | 32.5 |

It can be seen that a combination of a basic anion exchanger with activated carbon gives improved decolorization compared to the use of a single adsorbent.

EXAMPLE 3

The amount indicated in each case of 33% strength quench solution of TEDA in DPG having a color number of 401.7 APHA was admixed with the respective amount of adsorbent (combination of granulated carbon and anion exchanger) and shaken for 19 hours at 60° C. The results are shown in table 3.

TABLE 3

Color number of TEDA solutions in DPG after treatment with combinations of granulated carbons with basic anion exchangers

| Experiment | Amount of TEDA solution/g | Adsorbent | Amount/g | APHA color number obtained |
|---|---|---|---|---|
| A | 100.25 | PAK 1200 + Ambersep 900 OH | 1.010/4.020 | 47.3 |
| B | 100.27 | F300 + Ambersep 900 OH | 4.059/1.054 | 50.3 |
| C | 100.21 | CAL + Ambersep 900 OH | 1.068/4.031 | −37.9 |
| D | 100.12 | CPG LF 12 × 40 + Ambersep 900 OH | 4.066/1.099 | 46.3 |
| E | 100.29 | F400 + Ambersep 900 OH | 4.008/1.018 | 55.0 |

The example shows that color numbers of ≦50 APHA can be achieved using this method.

EXAMPLE 4

The experiment was carried out as described in example 3, but a TEDA/DGP solution having a color number of 843 APH was used. The results are shown in table 4.

TABLE 4

Color number of TEDA solutions in DPG after treatment with combinations of granulated carbons with basic anion exchangers

| Experiment | Amount of TEDA solution/g | Adsorbent | Amount/g | APHA color number obtained |
|---|---|---|---|---|
| A | 100.06 | PAK 1200 + Ambersep | 1.003/4.032 | 40.4 |

TABLE 4-continued

Color number of TEDA solutions in DPG after treatment with combinations of granulated carbons with basic anion exchangers

| Experiment | Amount of TEDA solution/g | Adsorbent | Amount/g | APHA color number obtained |
|---|---|---|---|---|
| B | 100.73 | F300 + Ambersep 900 OH | 4.012/1.078 | 52.9 |
| C | 100.58 | CAL + Ambersep 900 OH | 2.524/2.501 | 36.3 |
| D | 100.83 | CPG LF 12 × 40 + Ambersep 900 OH | 4.033/0.993 | 80.9 |
| E | 100.71 | F400 + Ambersep 900 OH | 4.048/1.012 | 40.9 |

The example shows that even at low color numbers of 843 APHA, final color numbers of ≦50 APHA can be achieved.

EXAMPLE 5

Quench solutions of TEDA in DPG were treated with various absorbents and the solutions obtained were subsequently stored. It is found that treatment with activated carbon and an anion exchanger gives a product which is stable on storage.

TABLE 5

Influence of the storage time on the APHA color number (storage under nitrogen, dark, at room temperature)

| Experiment | Adsorbent | Amount of absorbent/ 100 ml | T/° C. | APHA color number, immediate | APHA color number after storage | APHA color number after storage |
|---|---|---|---|---|---|---|
| A | PAK 1220 | 5 g | 25 | 69 | 93 (1 month) | 104 (2 months) |
| B* | 1) PAK 1200 | 5 g | 60 | 66 | | |
| | 2) Ambersep 900 OH | 5 g | 60 | 33 | 31 (1.5 months) | |
| C* | 1) Ambersep 900 OH | 5 g | 60 | 98 | 103 | |
| | 2) PAK 1220 | 5 g | 60 | 95 | (1.5 months) | |
| D | PAK 1220 + Ambersep 900 OH | 1 g/4 g | 60 | 47 | 49 (1 month) | |
| E | CAL + Ambersep 900 OH | 1 g/4 g | 60 | 38 | 40 (1 month) | |
| F | CPG LF 12 × 40 + Ambersep 900 OH | 1 g/4 g | 60 | 48 | 49 (1 month) | |

*Adsorbent 1 added first, followed by adsorbent 2

We claim:

1. A process for preparing TEDA solutions comprising a solvent selected from the group consisting of polyhydric alcohols and ethers of polyhydric alcohols, which comprises
    a) passing gaseous TEDA into the solvent,
    b) treating the solution with one or more suitable adsorbents.

2. A process as claimed in claim 1, wherein the adsorbents are selected from the group consisting of basic anion exchangers and activated carbons.

3. A process as claimed in claim 2, wherein the adsorbents are selected from the group consisting of strongly basic anion exchangers, granulated carbons and pulverulent carbons.

4. A process as claimed in claim 2, wherein the anion exchangers comprise $OH^-$, $Cl^-$ or $SO_4^{2-}$ anions.

5. A process as claimed in claim 2, wherein the activated carbon has a specific surface area of from 100 to 3000 $m^2/g$.

6. A process as claimed in claim 5, wherein the surface area is from 700 to 1500 $m^2/g$.

7. A process as claimed in claim 3, wherein a combination of a strongly basic anion exchanger and an activated carbon is used.

8. A process as claimed in claim 7, wherein the anion exchanger and the activated carbon are brought into contact with the TEDA solution either together or in the order 1) activated carbon, 2) anion exchanger.

9. A process as claimed in claim 1, wherein the solvent is selected from among ethanediol, 1,2-propanediol, 1,3-propanediol, 1,2-butanediol, 1,3-butanediol, 1,4-butanediol, glycerol, diethylene glycol, triethyleneglycol, dipropylene glycol, tripropylene glycol and trimethylolpropane and ethers of these alcohols with a lower monohydric alcohol.

10. A process as claimed in claim 9, wherein the ether of the monohydric alcohol is an ether of methanol.

11. A process as claimed in claim 9, wherein the solvent is selected from among ethanediol, 1,2-butanediol and dipropylene glycol.

12. A process as claimed in claim 1, wherein the gaseous TEDA is obtained by vaporization of crude TEDA.

13. A process as claimed in claim 1, wherein the adsorbent/adsorbents are regenerated after use.

14. A process as claimed in claim 13, wherein the regeneration is carried out by means of strong acids or strong caustic alkalis.

15. A process as claimed in claim 1, wherein the adsorbent is present in the form of a fixed bed, a suspended bed or a fluidized bed.

16. A process as claimed in claim 1, which is carried out continuously, batchwise or semicontinuously.

* * * * *